(12) United States Patent
Avitall

(10) Patent No.: US 10,631,927 B2
(45) Date of Patent: Apr. 28, 2020

(54) SMALL LOOP ABLATION CATHETER

(71) Applicant: Boaz Avitall, Milwaukee, WI (US)

(72) Inventor: Boaz Avitall, Milwaukee, WI (US)

(*) Notice: Subject to any disclaimer, the term of this patent is extended or adjusted under 35 U.S.C. 154(b) by 877 days.

(21) Appl. No.: 15/205,940

(22) Filed: Jul. 8, 2016

(65) Prior Publication Data

US 2016/0317223 A1    Nov. 3, 2016

Related U.S. Application Data

(62) Division of application No. 14/139,062, filed on Dec. 23, 2013, now abandoned.

(51) Int. Cl.
*A61B 18/12* (2006.01)
*A61B 18/14* (2006.01)
*A61B 18/00* (2006.01)

(52) U.S. Cl.
CPC .. *A61B 18/1492* (2013.01); *A61B 2018/0016* (2013.01); *A61B 2018/00023* (2013.01); *A61B 2018/00357* (2013.01); *A61B 2018/00577* (2013.01); *A61B 2018/00815* (2013.01); *A61B 2018/00839* (2013.01); *A61B 2018/1407* (2013.01); *A61B 2018/1467* (2013.01)

(58) Field of Classification Search
CPC ........ A61B 18/1492; A61B 2018/1407; A61B 2018/00577; A61B 2018/00357
See application file for complete search history.

(56) References Cited

U.S. PATENT DOCUMENTS

| | | | |
|---|---|---|---|
| 5,687,723 A | | 11/1997 | Avitall |
| 5,910,129 A | * | 6/1999 | Koblish ............. A61B 18/1492 604/159 |
| 6,579,288 B1 | * | 6/2003 | Swanson .......... A61B 17/00234 606/31 |
| 7,008,418 B2 | | 3/2006 | Hall et al. |
| 7,678,108 B2 | | 3/2010 | Chrisitian et al. |
| 7,850,685 B2 | | 12/2010 | Kunis et al. |
| 8,337,492 B2 | | 12/2012 | Kunis et al. |
| 2003/0181901 A1 | * | 9/2003 | Maguire ............. A61B 18/1492 606/41 |
| 2004/0143256 A1 | * | 7/2004 | Bednarek ........... A61B 18/1492 606/41 |
| 2011/0112524 A1 | * | 5/2011 | Stern ................. A61M 25/0147 606/33 |
| 2012/0109115 A1 | | 5/2012 | Condie et al. |
| 2012/0289982 A1 | * | 11/2012 | Gunday ......... A61B 17/320725 606/159 |
| 2015/0005762 A1 | * | 1/2015 | Belk .................... A61N 1/0551 606/41 |

* cited by examiner

*Primary Examiner* — Jaymi E Della

(57) ABSTRACT

A catheter system for creating lesions for the treatment of cardiac arrhythmias is disclosed that includes a catheter having a distal ablation segment that has an electrode array comprising a plurality of spaced ablation and recording electrode devices arranged in a tight loop configuration that is used to create a series of overlapping loop-shaped ablation footprints to produce a continuous lesion resembling a chain-link configuration.

7 Claims, 4 Drawing Sheets

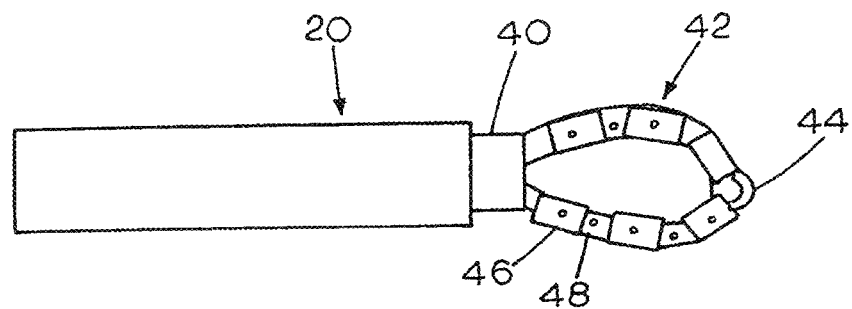
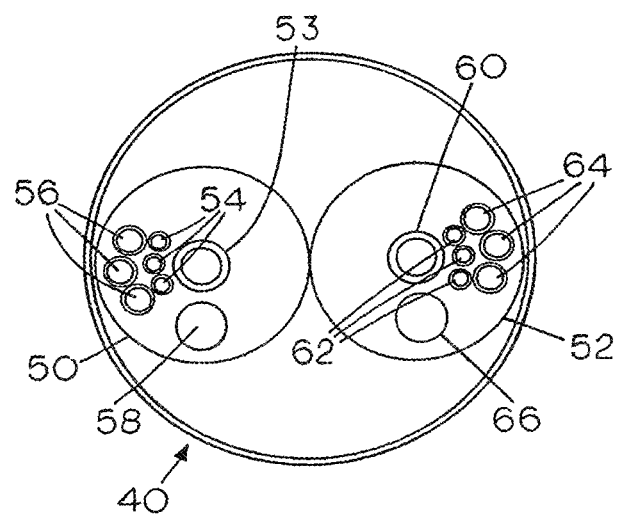
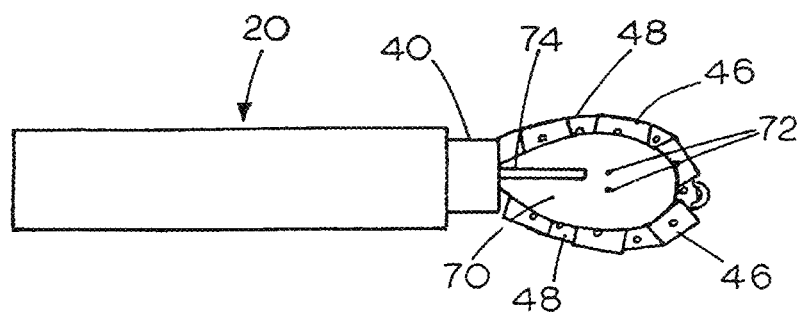

SMALL LOOP ABLATION CATHETER

CROSS-REFERENCE TO RELATED APPLICATIONS

The present application is a division of U.S. patent application Ser. No. 14/139,062, filed on Dec. 23, 2013, titled Small Loop Ablation Catheter.

STATEMENT REGARDING FEDERALLY SPONSORED RESEARCH OR DEVELOPMENT

Not applicable.

BACKGROUND OF THE INVENTION

I. Field of the Invention

The present invention relates generally to the field of catheter-based tissue ablation devices and techniques and, more particularly, to catheter devices and methods for performing tissue ablation to relieve atrial cardiac arrhythmias. Specifically, the invention provides a cure for atrial fibrillation by using transcutaneous transvascular catheter ablation in an overlapping pattern to produce the effect of the Cox Maze surgical procedure.

II. Related Art

Cardiac arrhythmias, particularly atrial fibrillation, are common and dangerous medical conditions causing abnormal, erratic cardiac function. Atrial fibrillation is observed particularly in elderly patients and results from abnormal conduction and automaticity in regions of cardiac tissue. Chronic atrial fibrillation (AF) may lead to serious conditions including stroke, heart failure, fatigue and palpitations. The treatment of chronic AF requires the creation of a number of transmural contiguous linear lesions. The use of a pattern of surgical incisions and thus surgical scars to block abnormal electrical circuits, and passageways known as the Cox Maze procedure, has become the standard surgical procedure for effective surgical cure of AF. The procedure requires a series of full-thickness incisions to isolate the pulmonary veins and the posterior wall of the left atria. Additional lines involve the creation of lesions from the posterior wall to the mitral valve, at the atrial isthmus line and superior vena cava (SVC) to the inferior vena cava (IVC) with a connection to the right atrial appendage.

Catheters have been developed that make the corrective procedure less invasive. They are designed to create lesions by ablation of tissue that performs the function of the surgical incisions. These include catheters that attempt to connect a series of local or spot lesions made using single electrodes into linear lesions. Devices that use a linear array of spaced electrodes or electrodes that extend along the length of a catheter have also been used.

Important drawbacks found fundamental in the current catheter-based ablation approaches can be attributed to several factors including a lack of consistent contact between the ablation devices and the target tissues, an inability to accurately evaluate lesion maturation, and the inability to connect lesions in a manner so as to create a continuous transmural line that produces a continuous electrical conduction block. Therefore, there remains a need for improved ablation devices and procedure techniques.

SUMMARY OF THE INVENTION

By means of one aspect of the present inventive concept, there is provided an ablation catheter to enable an operator to treat a patient suffering from an arrhythmia by employing an overlapping ablation technique that increases the ablation footprint and produces more reliable continuous lesions that prevent reconnection of electrical pathways in cardiac tissue.

The catheter system, which may be exemplified in a number of embodiments, includes an outer multi-directional deflection sheath in the form of an elongate flexible, steerable sheath member having a proximal end and a distal end. A lumen extends between the proximal and distal ends. A catheter including an elongate outer shaft and an elongate torqueable central control shaft core coaxially received in the outer catheter shaft is disposed in the outer sheath lumen and is in slidable relation with respect thereto. Certain embodiments may have a plurality of central control shafts as will be described.

The distal portion of the catheter includes an ablation segment having a plurality of electrodes forming a combined electrode array that includes an array of sequentially arranged, spaced ablation electrodes and an array of spaced recording and thermistor electrodes. The combined electrode array is designed to be formed in a tight loop configuration for an ablation procedure. The array of spaced recording and thermistor electrodes may preferably be interspersed with the ablation electrodes. The ablation electrodes are preferably operated by radio frequency (RF) power.

In some embodiments, the ablation segment, with the combined electrode array, is initially arranged as a generally linear extension of the distal portion of the catheter and is provided with a distal pull wire-type device that extends proximally such that it can be caused to be retracted from the proximal end of the sheath. This causes the attached electrode array to assume a loop configuration, the size of which can be adjusted as needed. Alternatively, the ablation segment may be arranged in a fixed tight loop with both ends attached to the catheter shaft having a collapsible configuration which can be squeezed together to be accommodated in a corresponding sheath, which may require a slightly larger diameter, possibly about 9.5 F vs 8 F, for this embodiment. Further embodiments may incorporate an electroded central membrane associated with the loop. The central membrane insulates adjacent blood from the procedure and may also be provided with recording, temperature sensing and pacing devices to monitor lesion formation and maturation. Irrigation may also be provided via the membrane.

The catheter further preferably incorporates an irrigation system that supplies irrigation fluid to cool the electrodes and prevent char formation. The system is configured to allow equal flushing of each of the plurality of ablation electrodes during the ablation procedure. Fluid is supplied through one or more irrigation channels in the catheter shaft and connections to the electrodes. The catheter shaft, of course, also accommodates conductors attached to each ablation and recording electrode.

Preferred formed ablation loops in accordance with the invention may be various sizes, but they are generally defined as "small loops" which may have a nominal width from about 10 mm to 20 mm and a nominal length from about 20 mm to 30 mm. A preferred size is about 15 mm wide by about 25 mm long.

BRIEF DESCRIPTION OF THE DRAWINGS

In the drawing figures wherein like numerals depict like parts throughout the same:

FIG. 3 illustrates a view similar to FIGS. 1A and 1B in an embodiment of the invention in which the ablation segment is in the form of a fixed loop attached to the distal end of the catheter;

FIG. 4 is a schematic cross sectional representation of the catheter shaft of FIG. 3;

FIG. 5 depicts a schematic view of an embodiment similar to that of FIGS. 3 and 4 wherein the center of the loop is covered with a membrane;

DETAILED DESCRIPTION

The following detailed description pertains to several embodiments that feature aspects of the concepts of the present development. These embodiments are meant as examples and are not intended to limit the scope of the present invention in any manner.

The present invention provides catheters useful for evaluating tissue temperature and conduction, and for performing targeted tissue ablation procedures. The catheters include an outer sheath having an elongated tubular body that includes a proximal and a distal end and a lumen extending the length of the sheath for receiving a catheter in slidable relation in the lumen. The catheters are generally of a type used for performing intracardiac procedures and are preferably introducible through a previously-placed sheath that had been inserted into the femoral vein and maneuvered via the Inferior vena cava (IVC). For ablation in the left atria, the sheath is guided first into the right atria. Under intracardiac ECHO visualization, or the like, the deflectable sheath is caused to penetrate the intra-atrial septum and the sheath is then positioned in the left atria. The ablation catheter is then introduced through the sheath and delivered to the left atria via the sheath. The catheter has a steerable tip that allows it to be precisely positioned as required for the ablation procedure. The catheter includes ablation elements mounted on a distal ablation segment designed to be utilized in a tight loop formation. The ablation segment contains electrode elements designed to both ablate and map the electrical activity of tissue. The array must be sufficiently stiff in use such that it may be applied with sufficient force against tissue to be ablated.

Generally, after performing an electrical mapping procedure, the operator positions the ablation electrode loop as desired and utilizes energy provided by an external source such as radio frequency (RF) energy to ablate the tissue in desired areas. The goal of the catheter ablation procedure is to permanently disrupt the electrical pathways in cardiac tissue to stop the emission and propagation of erratic electrical impulses in the tissue. Once ablated, the tissue no longer conducts such impulses.

The catheters of the present invention are configured to accomplish the mapping and ablation procedure utilizing an array of electrodes arranged in a tight loop, which may be formed by the use of a distally connected pull wire which deflects a basically linear arrangement of electrodes into a loop or by the use of a fixed loop at the distal end of the catheter. As will be discussed, the use of a tight loop enables the establishment of a series of overlapping loop-shaped lesions that produce a continuous "chain link" footprint that greatly improves linear continuity in the lesion.

Figure 1A:
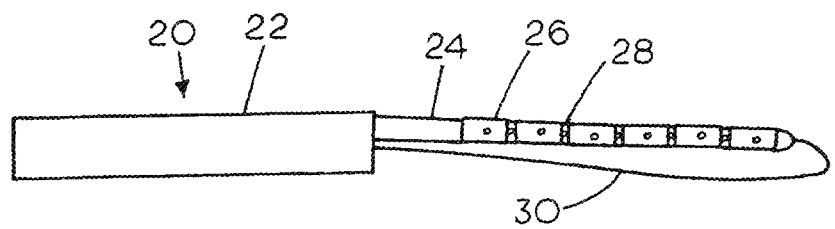
FIG. 1A depicts a fragmentary schematic view illustrating the distal end of an ablation catheter system in accordance with the invention having an ablation segment that is arranged for transport in a sheath as a generally linear extension of the distal portion of the catheter.
Figure 1B:
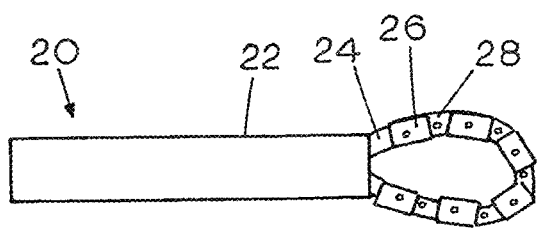
FIG. 1B depicts the embodiment of FIG. 1A with the ablation segment pulled into a loop configuration by a pull wire.

FIGS. 1A and 1B depict fragmentary schematic views illustrating the distal end of an ablation catheter system in accordance with the invention. The system is shown generally at 20 and includes an outer steerable and deflectable sheath 22 and catheter shaft 24. An ablation segment is attached to the distal end of the catheter shaft and is shown with a linear array of spaced electrode devices, including radio frequency (RF) ablation electrodes 26 and interspersed recording/thermistor pin-type electrodes 28, which function as temperature sensors, determine tissue contact, evaluate lesion maturation, map and record conduction with high fidelity. An attached pull wire is shown at 30. The ablation electrodes 26, which may be platinum or platinum alloy wound wire, for example, are typically about 6 F in width by about 6 mm long and spaced about 2 mm apart. The example shown in FIGS. 1A and 1B incorporates a distal ablation segment that has a total length of about 50 mm. The recording/thermistor electrodes are about 1 mm$^2$ in size.

The loop shown in FIG. 1B is formed by retracting the pull wire 30 which extends to the proximal end of the sheath 22. The loop size can readily be adjusted by advancing the catheter shaft in the sheath to maximize the loop size or by retracting the catheter shaft to withdraw part of the ablation segment into the catheter to shrink the size of the loop.

Figure 2:
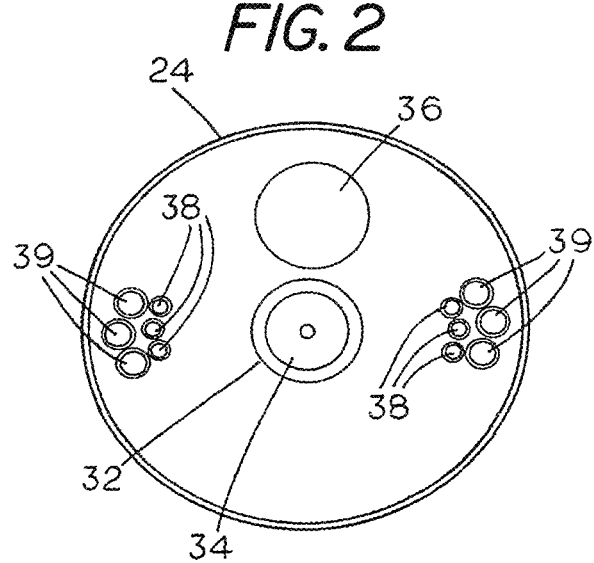
FIG. 2 is a greatly enlarged schematic cross section view of the main catheter shaft of the embodiment of FIGS. 1A and 1B.

FIG. 2 is a greatly enlarged schematic cross sectional view of the main catheter shaft of the embodiment of FIGS. 1A and 1B. The catheter shaft includes a central control shaft of variable stiffness 32 with core 34 and a hollow irrigation tube 36. Recording and thermistor electrical conductors are shown at 38 and ablation electrode conductors are depicted at 39. The irrigation tube 36 is connected to each of the ablation electrodes 26 by branch connectors that are configured to supply like amounts of irrigation or cooling fluid to each of the ablation electrodes.

A slightly different embodiment is shown in the fragmentary schematic view of FIG. 3 in which a different configuration of a catheter shaft 40 is provided with a fixed loop ablation segment 42 that is attached at both ends to the catheter shaft 40. The loop includes a soft collapsible nose segment 44, ablation electrodes 46 and recording/thermistor electrodes 48. The soft collapsible nose segment 44 permits the ablation loop to be compressed and inserted into the sheath for transport. The distal end of the catheter shaft 40 is provided with a deflection capability to add additional degrees of freedom and flexibility to the deflection capability of the sheath in maneuvering the loop during a procedure.

FIG. 4 depicts a schematic cross sectional representation of the catheter shaft of the embodiment of FIG. 3. The main catheter shaft 40 includes a pair of spaced internal loop shaft members 50 and 52, one connected to each side of the fixed loop ablation segment 42. The shaft 50 includes a variable stiffness shaft and core 53 that is independently torqueable, recording/thermistor electrode conductors 54, ablation electrode conductors 56 and an irrigation tube 58 that supplies irrigation fluid to cool the electrode of the corresponding side of the fixed loop ablation segment, each ablation electrode having an irrigation port. The internal shaft member 52 contains the same devices and these include independently torqueable shaft and core 60, recording/thermistor electrode conductors 62, ablation electrode conductors 64 and irrigation tube 66 that service the other corresponding section of the fixed loop ablation segment 42. Thus, the irrigation connections and electrical connections enter the loop from both ends.

As with the previous embodiment, the irrigation channels enable the flushing of the ablation electrodes during the application of RF power and low level irrigation to maintain the integrity of the associated irrigation ports at other times. The ablation electrodes may be wire wound sections, each containing an irrigation port supplied by an irrigation conduit supplied from a main irrigation tube. The irrigation system is designed so that the most distal electrode receives the same irrigation pressure as the most proximal. This may be done by well-known techniques to adjust the flow resistance.

FIG. 5 shows a schematic view of a fixed loop catheter embodiment similar to that shown in FIGS. 3 and 4, but in which the open center portion of the loop is covered with a membrane 70. The membrane is provided with additional sensing/pacing electrodes as at 72 and an irrigation tube 74. The membrane allows an amount of irrigation fluid to accumulate within the enclosed space under the membrane when the loop is pressed against tissue during ablation. The membrane insulates the tissue being ablated from circulating blood and allows accurate tissue heating. The recording and pacing capability permits monitoring of lesion formation and accurate assessment of tissue electrical isolation post ablation. Pacing can be used during the ablation process as it has been found that, when cardiac pace capture is lost during ablation, that signifies completion of a lesion.

Figure 6:
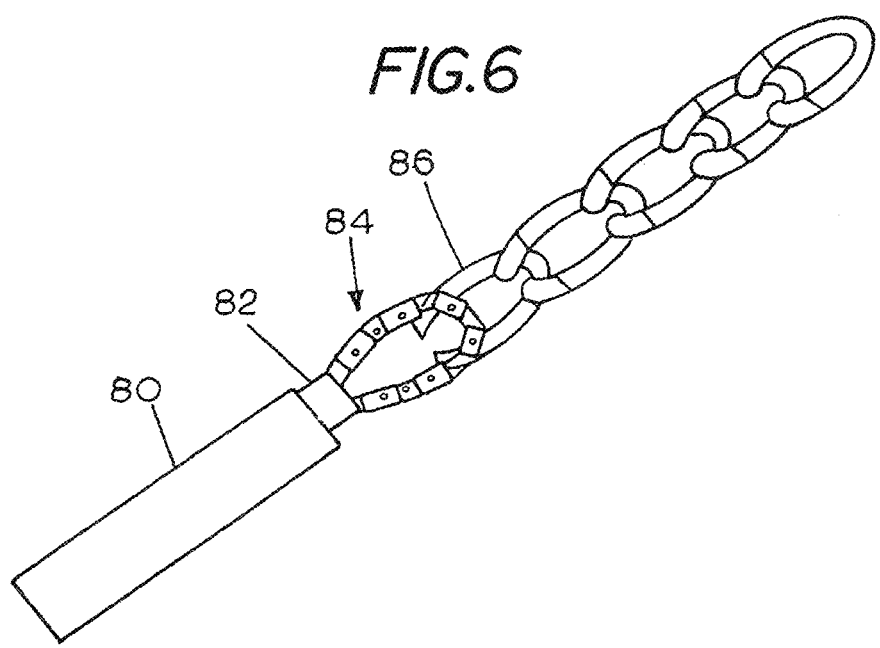
FIG. 6 illustrates the creation of a chain link lesion.

FIG. 6 illustrates the creation of a chain link lesion. A sheath fragment is shown at 80, carrying associated catheter 82 with ablation segment 84 is used repeatedly in overlapping fashion to create a series of overlapping ablation links as footprints 86. The links may be any desired size and typical links as illustrated are about 10 mm wide by 15 mm long and overlapped to produce a continuous "chain link" lesion.

Figure 7:
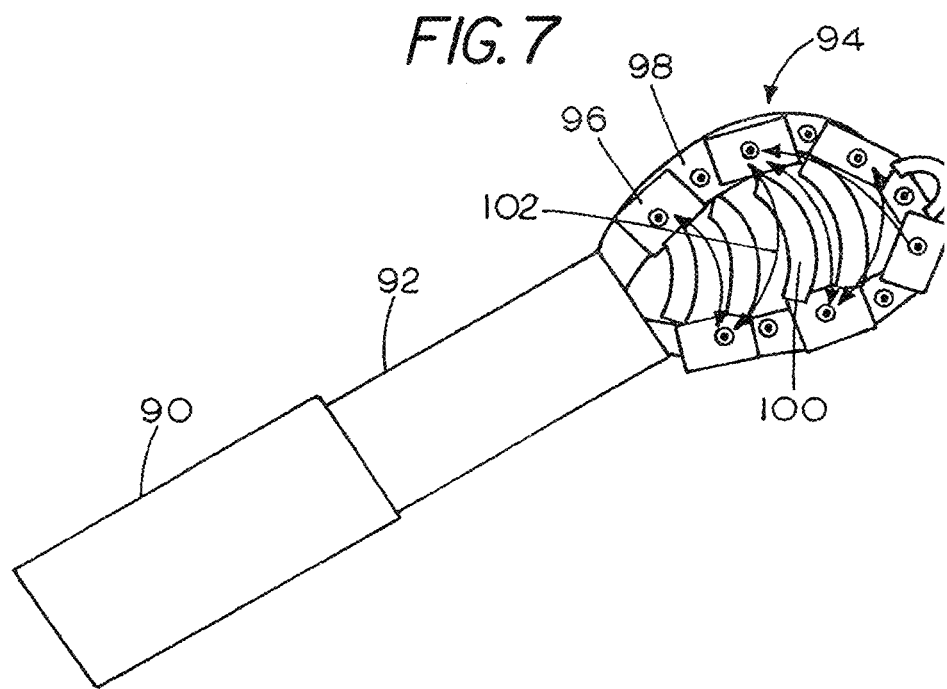
FIG. 7 illustrates the bulging of tissues encircled by the loop of a catheter in accordance with the invention as it is compressed into tissue to be ablated.

FIG. 7 schematically illustrates an effect of compression of the loop into adjacent tissue which results in a corresponding bulging of the tissues encircled by the loop, particularly at the center of the loop. The figures includes a multi-directional deflectable sheath fragment 90 with extended distal catheter at 92 and a catheter ablation segment formed into a loop at 94 with ablation electrodes 96 and recording/thermistor devices 98 arranged as in previous embodiments. The bulging of the tissue is illustrated by curved segment 100 and inter-ablation electrode conduction paths are illustrated by the lines 102, which indicate the use of a bipolar technique. The bulging of the tissue at the center of the loop has been found to enable bipolar RF current to more effectively ablate the tissue in accordance with the operation of the loop ablation catheter of the invention.

Figure 8:
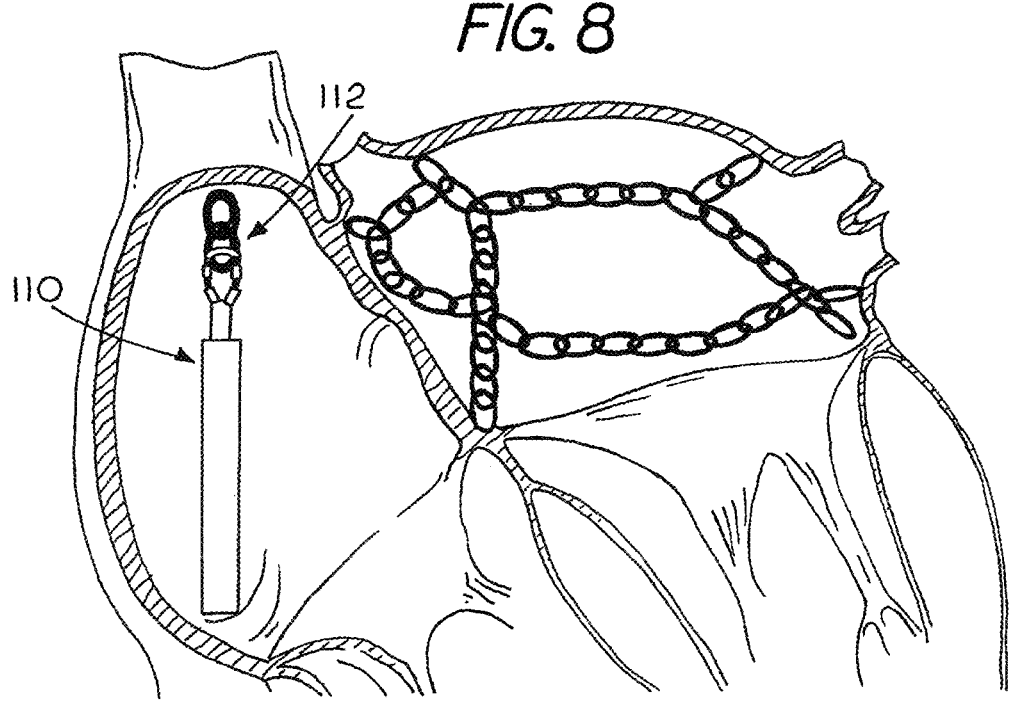
FIG. 8 is a partial internal representation of a heart illustrating a left atrial lesion set directed at the isolation of the pulmonary veins, isolation of the left atrial posterior wall and septal, as well as the left atrial isthmus.
Figure 9:
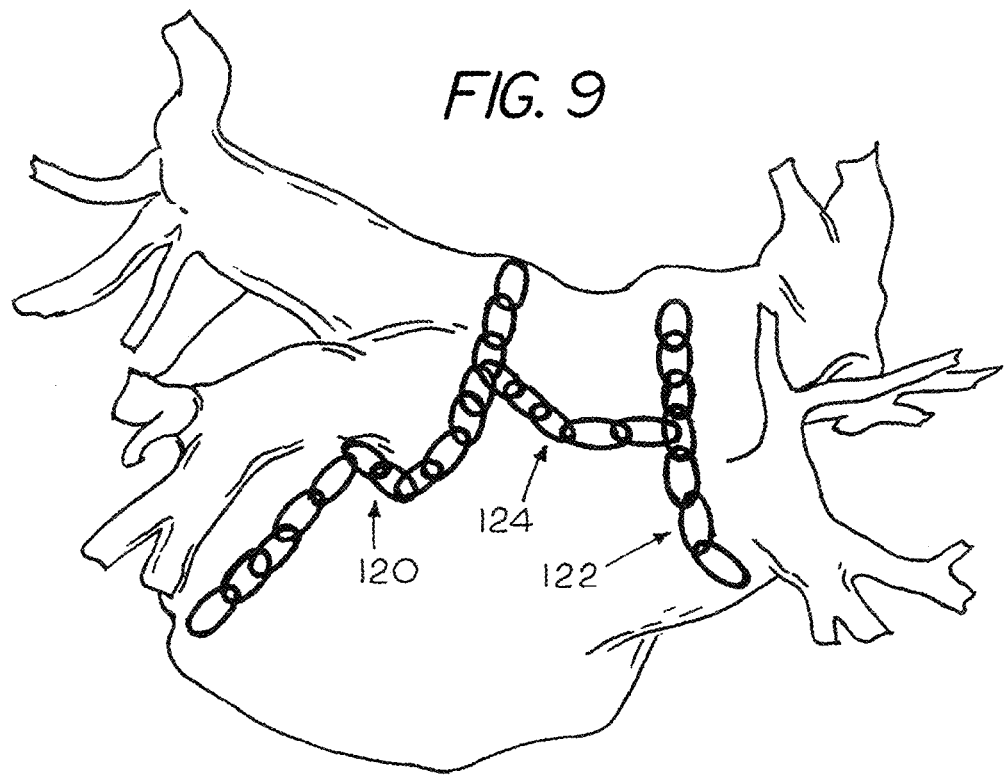
FIG. 9 is a computed tomography scan of a left atrial lesion set directed at the isolation of the pulmonary veins (2 veins at a time) and a connecting lesion between the pulmonary vein isolation lesions and the left atrial isthmus lesion.

FIGS. 8 and 9 illustrate lesion sets formed by utilizing the chain link technique of the present invention. In FIG. 8, the left atrial lesion set is directed at isolation of the pulmonary veins, isolation of the left atrial posterior wall and septal, as well as the left atrial isthmus. In the right atrium, there is shown a catheter system 110 in the process of creating an intracaval lesion at 112.

In FIG. 9, there is shown a computer tomography scan of a left atrial lesion set which is directed at the isolation of the pulmonary veins (two veins at a time) at 120 and 122. A connecting lesion between the pulmonary vein isolation lesions in the left atrial isthmus lesion is shown at 124.

It should be noted that the term "ablation" or "ablation procedures" refers to procedures in which tissue is destroyed in a manner that disconnects or isolates pathways of abnormal electrical activity. The term "ablation electrode" refers to an energy delivery element used to deliver electrical energy such as RF energy. The high concentration of energy near the electrode results in localized tissue ablation. The energy delivery can be monopolar or bipolar. With bipolar energy delivery, the energy is conducted from one electrode to one or more other electrodes in an array of associated electrodes. Bipolar energy delivery enables closer control of the amount of tissue ablated and is, therefore, preferred for the loop catheter of the present invention. The timing of the application of the energy may also be varied and may controlled by temperature feedback from sensor electrodes which may also be used to record and map electrical activity in the tissue. RF electrodes may be constructed from platinum or a platinum alloy that may be in the form of a solid member or, preferably, a wire coil.

It should be recognized that the pattern of ablated tissue created by the incremental use of the small loop catheter of the present invention leaves little possibility for gaps in a desired lesion pattern as it provides a series of overlapping footprints that give more reliable results than a series of spaced electrodes.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

What is claimed is:

1. A method of creating a continuous lesion for the treatment of cardiac arrhythmias comprising:
   providing a catheter having a distal ablation segment having an electrode array comprising a plurality of spaced ablation and recording electrode devices arranged in a tight loop configuration wherein said catheter further incorporates an irrigation system configured to allow flushing of said electrode array;
   using said distal ablation segment in a procedure to create a series of at least three overlapping loop-shaped ablation footprints where a first loop shaped footprint overlaps a second loop shaped footprint and the second loop shaped footprint overlaps a third loop shaped footprint to create the continuous lesion in a heart chamber resembling a chain-link configuration while using irrigation fluid to cool said plurality of spaced ablation and recording electrode devices to prevent tissue overheating during ablation as needed.

2. The method of claim 1 wherein said plurality of spaced ablation and recording electrode devices in said electrode array are operated using radio frequency (RF) energy in a bipolar mode to limit lesion formation to tissue enclosed by the tight loop configuration.

3. The method as in claim 1 further comprising monitoring said continuous lesion formation and evaluating a maturation of tissue ablation of said series of overlapping loop-shaped ablation footprints.

4. The method as in claim 1 wherein said procedure includes isolation of pulmonary veins in the heart chamber wherein the heat chamber is a left atrium of a heart.

5. The method as in claim 4 further comprising providing a left atrial isthmus lesion and a connecting lesion between lesions isolating said pulmonary veins in the left atrium of the heart and the atrial isthmus lesion.

6. The method as in claim 3 wherein said monitoring and evaluating involves recording and temperature sensing technology.

7. The method as in claim 1 and further including the step of providing a membrane barrier layer affixed to the tight loop configuration in covering relation with respect to a central opening of said tight loop configuration and said irrigation system being arranged for injecting the irrigation fluid in a space defined by the tight loop configuration and between the membrane barrier layer and cardiac tissue, the membrane barrier layer isolating the cardiac tissue overlaid by the tight loop configuration from blood present in the heart chamber and wherein the membrane barrier layer further supports pacing and recording electrodes for assessing a quality of tissue isolation achieved by the continuous lesion.

* * * * *